(12) United States Patent
Nguyen et al.

(10) Patent No.: US 7,316,044 B1
(45) Date of Patent: Jan. 8, 2008

(54) TOOTHBRUSH HAVING COUNTER-ROTATING HEADS

(76) Inventors: Huy Nguyen, 3880 Duke of York Boulevard, Unit 710, Mississauga, Ontario (CA) L5B-4M7; Cuong Nguyen, 3880 Duke of York Boulevard, Unit 710, Mississauga, Ontario (CA) L5B-4M7

( * ) Notice: Subject to any disclaimer, the term of this patent is extended or adjusted under 35 U.S.C. 154(b) by 246 days.

(21) Appl. No.: 11/248,799

(22) Filed: Oct. 13, 2005

(51) Int. Cl.
*A61C 17/26* (2006.01)

(52) U.S. Cl. .......................................................... 15/23

(58) Field of Classification Search ............... 15/23
See application file for complete search history.

(56) References Cited

U.S. PATENT DOCUMENTS

| | | | |
|---|---|---|---|
| 52,385 A | 2/1866 | Carr | |
| 2,124,145 A * | 7/1938 | Merkel, Jr. ..................... | 15/23 |
| 2,583,886 A * | 1/1952 | Schlegel ........................ | 15/23 |
| 2,655,675 A * | 10/1953 | Grover ........................... | 15/23 |
| 3,258,802 A * | 7/1966 | Rodriguez ..................... | 15/23 |
| 4,131,967 A | 1/1979 | Northemann et al. | |
| 4,603,448 A * | 8/1986 | Middleton et al. ........... | 15/22.1 |
| D297,888 S | 10/1988 | Stoll | |
| 4,776,054 A | 10/1988 | Rauch | |
| 5,353,460 A | 10/1994 | Bauman | |
| 5,359,747 A | 11/1994 | Amakasu | |
| 5,428,855 A * | 7/1995 | Li ................................. | 15/23 |
| 5,864,911 A * | 2/1999 | Arnoux et al. ................ | 15/23 |
| 6,381,794 B1 | 5/2002 | Porper et al. | |
| 6,401,288 B1 | 6/2002 | Porper et al. | |
| 2005/0144745 A1* | 7/2005 | Russell ......................... | 15/23 |

FOREIGN PATENT DOCUMENTS

EP 488971 * 6/1992

* cited by examiner

*Primary Examiner*—Mark Spisich
(74) *Attorney, Agent, or Firm*—Donald R. Schoonover

(57) ABSTRACT

An electric toothbrush has bristle heads that rotate counter to each other. The toothbrush operates from a battery stored in the handle section of the toothbrush.

1 Claim, 1 Drawing Sheet

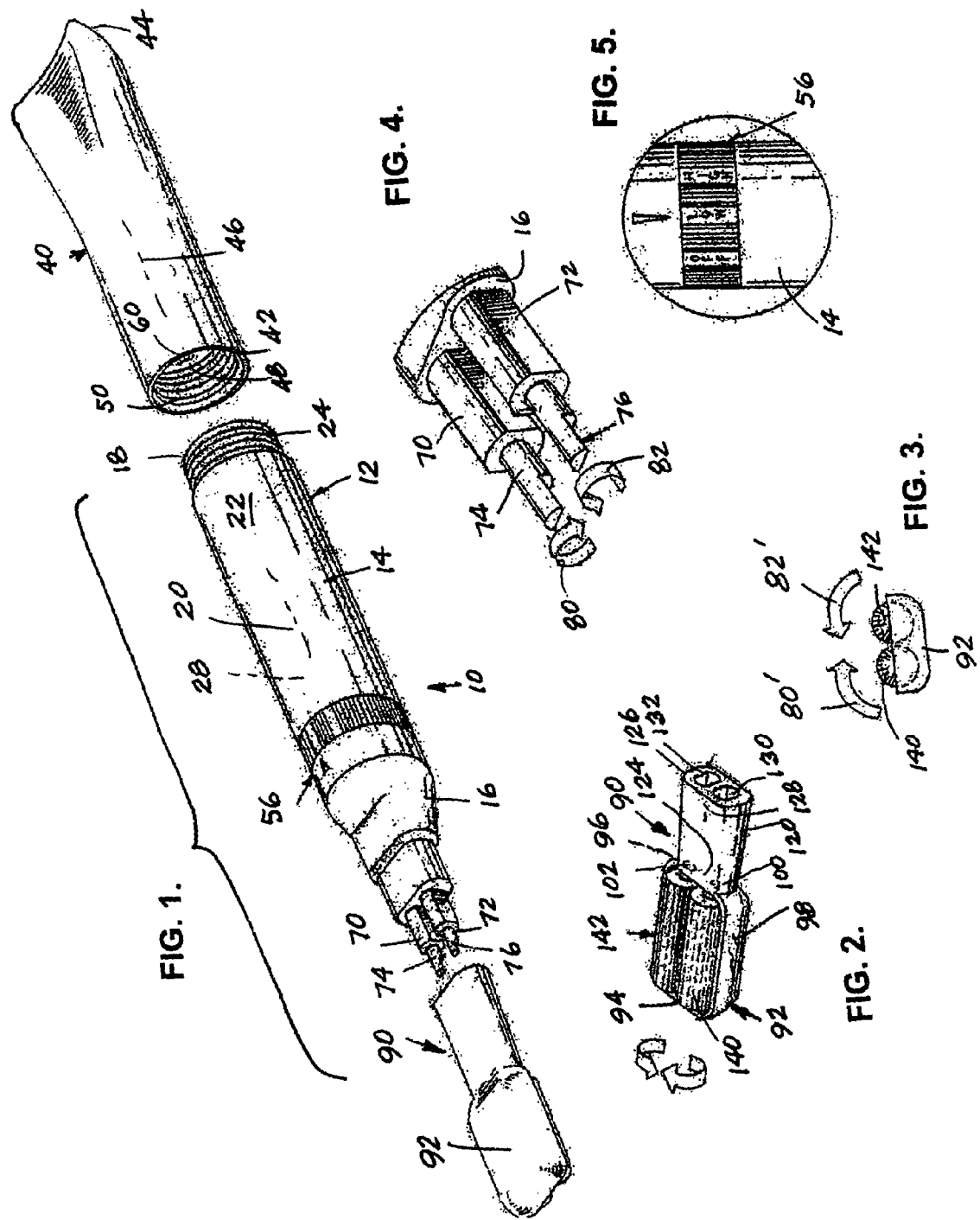

TOOTHBRUSH HAVING COUNTER-ROTATING HEADS

BACKGROUND OF THE INVENTION

1. Field of the Invention

The present invention relates to the general art of toothbrushes, and to the particular field of electric toothbrushes.

2. Description of the Related Art

The use of manual toothbrushes has, of course, been known for many years. Indeed, the use of mechanical toothbrushes, typically those which are electrically driven, has been known for a number of years. The purpose, in any event, is to clean the teeth, usually with a toothbrush which comprises a plurality of bristles that are used in conjunction with a dentifrice. Very often, the dentifrice is mildly abrasive.

The dental profession has propounded, for many years, a technique known as the "Bass Technique" which, if properly performed, is said to achieve superior results in terms of cleaning one's teeth using a manual toothbrush. Essentially, the Bass Technique requires the user to position a manual toothbrush over a zone of the teeth, and then to use very short stokes so as to more or less vibrate the brush at that zone where the brush has been located. This short-stroke brushing should continue for a period of time—typically, twenty to forty strokes—so as to remove any foreign material from that zone. The brush is then repositioned and typically another twenty to forty short strokes are performed. Because each zone is very small, the Bass Technique can be very time-consuming. Moreover, since it is a requirement that the strokes be very short which, in turn, requires excellent muscle control, exercising the Bass Technique can be very tiring.

The theory is that, at the end of any given stroke, the bristles will flex so as to become oriented in such a manner that the ends of the bristles point generally away from the direction of the travel of the bristles across the teeth. However, at the beginning of the next stroke, in the opposite direction, the still-flexed bristles will then be pointed in the direction of the stroke and this may cause the bristle to chisel the foreign material away from the teeth for a moment before the bristle again begins to flex so as to sweep across the surface of the tooth in the zone where it is located.

However, a more efficacious manner for brushing teeth comprises a variation of the Bass Technique, whereby oscillatory movement is imparted to a toothbrush. Of course, such oscillatory movement is not capable of being executed manually.

Apart from the removal of leftover food particles and the like, a particular purpose for cleaning the teeth is to remove plaque build-up from the teeth. Typically, when using a manual toothbrush, plaque build-up is removed much more easily from the buccal surfaces of the teeth than from the lingual surfaces of the teeth, with relatively good foreign material removal from the occlusal surfaces of the teeth also being achieved.

One development that has occurred in respect of manual toothbrushes is the provision of twin-headed brushes, whereby the lingual and buccal surfaces of the tooth can be scrubbed using the bristles of the brush at the same time, with the same stroking action of the brush.

As to electric toothbrushes, most electric toothbrushes provide groups of bristles which are located in concentric circles, where the brush head thus provided is rotated or, more usually, it is reciprocally rotated.

While electric toothbrushes are more efficient than manual toothbrushes, there is a need for an electric toothbrush which is even more efficient than known electric toothbrushes.

PRINCIPAL OBJECTS OF THE INVENTION

It is a main object of the present invention to provide an electric toothbrush which is even more efficient than known electric toothbrushes.

SUMMARY OF THE INVENTION

These, and other, objects are achieved by a toothbrush that has two counter-rotating heads. The heads have bristles thereon and the counter-rotation improves the cleaning efficiency of the toothbrush.

BRIEF DESCRIPTION OF THE DRAWING FIGURES

FIG. 1 is an exploded perspective view of a toothbrush embodying the present invention.

FIG. 2 is a perspective view of a head portion of the toothbrush embodying the present invention and showing the counter-rotating dual heads of the toothbrush.

FIG. 3 is an end elevational view of the head shown in FIG. 2.

FIG. 4 is a detailed view of the counter-rotating axles used in the toothbrush.

FIG. 5 is a detailed view of the control switch on the body of the toothbrush.

DETAILED DESCRIPTION OF THE PREFERRED EMBODIMENT

Other objects, features and advantages of the invention will become apparent from a consideration of the following detailed description and the accompanying drawings.

Referring to the Figures, it can be understood that the present invention is embodied in a toothbrush 10 that achieves the above-stated objectives.

Toothbrush 10 comprises a hollow body 12 having a first portion 14 which includes a first end 16 which is a front end when body 12 is in use, a second end 18, and a longitudinal axis 20 which extends between first end 16 and second end 18.

First portion 14 further includes an outer surface 22.

A screw thread 24 is defined on outer surface 22 of first portion 14 adjacent to second end 18, and an interior volume 28 is defined in first portion 14.

Body 12 further includes a second portion 40 which has a first end 42 which is located adjacent to second end 18 of first portion 14 when body 12 is in use. Second portion 40 further includes a second end 44 which is a rear end when body 12 is in use, and a longitudinal axis 46 which extends between first end 42 and second end 44. Longitudinal axis 46 of second portion 40 is co-linear with longitudinal axis 20 of first portion 14 when body 12 is in use.

An inner surface 48 is defined on second portion 40 and a screw thread 50 is defined on inner surface 48 of the second portion 40 adjacent to first end 42 of the second portion 40. Screw thread 50 on the second portion 40 is adapted to matingly engage screw thread 24 on first portion 14 when body 12 is in use.

A control switch 56 is mounted on first portion 14 and is used to control operation of toothbrush 10 in a manner known to those skilled in the art.

A power source, such as a rechargeable battery 60, or the like, is located in second portion 40.

First and second electric motors 70 and 72 are located on first portion 14 of body 12. Each motor 70, 72 includes a drive shaft, such as drive shaft 74 of motor 70 and drive shaft 76 of motor 72, that extends out of first end 16 of first portion 14.

The electric motors 70, 72 are arranged to rotate the drive shafts 74, 76 in opposite directions when activated whereby drive shaft 74 of the first motor rotates clockwise in direction 80 with regard to longitudinal axis 20 of the first portion 14 of body 12 and drive shaft 76 of second motor 72 rotates counterclockwise in direction 82 with regard to longitudinal axis 20. Each of the electric motors 70, 72 is electrically connected to control switch 56 to be electrically connected to the power source 60 via the control switch 56 to be activated when the control switch 56 is in an "on" condition as will be understood by those skilled in the art based on the teaching of the present disclosure.

A head unit 90 is mounted on first end 16 of the first portion 14 of body 12 when in use. Head unit 90 includes a C-shaped body section 92 which has a first end 94, a second end 96, and a longitudinal axis 98 which extends between first end 94 and second end 96 and which is co-linear with longitudinal axis 20 of first portion 14 of body 12 when in use.

Two holes 100 and 102 are defined through second end 96 of C-shaped body section 92.

A neck section 120 is located on second end 96 of the C-shaped body section 92 and has a first end 124 unitary with second end 96 of the C-shaped body section 92, a second end 126, and a longitudinal axis 128 which extends between first end 124 and second end 126 and which is co-linear with longitudinal axis 98 of the C-shaped body section 92.

First and second bores 130 and 132 extend through neck section 120 from first end 124 to second end 126. The bores 130, 132 of the neck section 120 are located to receive the drive shafts 74, 76 of the first and second motors 70, 72 so those drive shafts 74, 76 will extend through the neck section 120 and through holes 100 and 102 defined through the second end 96 of the C-shaped section 92 and into the C-shaped body section 92.

First and second cylindrical brushes 140 and 142 are mounted on respective drive shafts 74, 76 of the electric motors 70, 72 for rotation therewith. The cylindrical brushes 140, 142 are positioned in the C-shaped body section 92 and rotate in opposite directions as indicated by arrows 80' and 82' whereby, when motors 70 and 72 are activated, first cylindrical brush 140 rotates clockwise with regard to longitudinal axis 20 of first portion 14 of body 12 and second brush 142 rotates counterclockwise with regard to longitudinal axis 20 of the first portion 14 of the body 12.

It is to be understood that while certain forms of the present invention have been illustrated and described herein, it is not to be limited to the specific forms or arrangements of parts as described and shown.

What is claimed and desired to be covered by Letters Patent:

1. A toothbrush comprising:
   (a) a hollow body having
      (1) a first portion having
         (A) a first end which is a front end when said body is in use,
         (B) a second end,
         (C) a longitudinal axis which extends between the first end of the first portion and the second end of the first portion,
         (D) an outer surface,
         (E) a screw thread defined on the outer surface of the first portion adjacent to the second end of the first portion, and
         (F) an interior volume,
      (2) a second portion having
         (A) a first end which is located adjacent to the second end of the first portion when said body is in use,
         (B) a second end which is a rear end when said body is in use,
         (C) a longitudinal axis which extends between the first end of the second portion and the second end of the second portion, the longitudinal axis of the second portion being co-linear with the longitudinal axis of the first portion when said body is in use,
         (D) an inner surface,
         (E) a screw thread defined on the inner surface of the second portion adjacent to the first end of the second portion, the screw thread on the second portion being adapted to matingly engage the screw thread on the first portion when said body is in use, and
      (3) a control switch mounted on the first portion;
   (b) a power source located in the second portion of said body;
   (c) first and second electric motors located on the first portion of said body, each motor including a drive shaft that extends out of the first end of the first portion, said electric motors being arranged to rotate the drive shafts in opposite directions when activated whereby the drive shaft of the first motor rotates clockwise with regard to the longitudinal axis of the first portion of said body and the drive shaft of the second motor rotates counterclockwise with regard to the longitudinal axis of the first portion of said body, each of said electric motors being electrically connected to the control switch mounted on the first portion of said body to be electrically connected to the power source via the control switch to be activated when the control switch is in an "on" condition;
   (d) a head unit mounted on the first end of the first portion of said body when in use, said head unit including
      (1) a C-shaped body section having
         (A) a first end,
         (B) a second end,
         (C) a longitudinal axis which extends between the first end of the C-shaped body and the second end of the C-shaped body and which is co-linear with the longitudinal axis of the first portion of said body when in use, and
         (D) two holes defined through the second end of the C-shaped body section,
      (2) a neck section on the second end of the C-shaped body section and having
         (A) a first end unitary with the second end of the C-shaped body section,
         (B) a second end and a longitudinal axis which extends between the first end of the neck section and the second end of the neck section and which is co-linear with the longitudinal axis of the C-shaped body section, and (C) first and second bores extending through the neck section from the first end of the neck section to the second end of the neck section, the bores of the neck section being located to receive the drive shafts of the first and second motors so those drive shafts will extend through the neck section and through the holes defined through the second end of the C-shaped section and into the C-shaped body section; and (e) first and second cylindrical brushes, each brush being mounted on a drive shaft of one of the electric motors for rotation therewith, said cylindrical brushes being positioned in the C-shaped body section and rotate in opposite directions whereby when the motors are activated the first cylindrical brush rotates clockwise with regard to the longitudinal axis of the first portion of said body and the second brush rotates counterclockwise with regard to the longitudinal axis of the first portion of said body.

* * * * *